(12) United States Patent
Davis et al.

(10) Patent No.: US 10,100,277 B2
(45) Date of Patent: *Oct. 16, 2018

(54) PLURIPOTENT STEM CELL EXPANSION AND PASSAGE USING A STIRRED TANK BIOREACTOR

(71) Applicant: General Electric Company, Schenectady, NY (US)

(72) Inventors: Brian Michael Davis, Albany, NY (US); Kenneth Roger Conway, Clifton Park, NY (US); Xiaohua Zhang, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/075,211

(22) Filed: Mar. 21, 2016

(65) Prior Publication Data

US 2016/0215257 A1 Jul. 28, 2016

Related U.S. Application Data

(63) Continuation-in-part of application No. 14/956,408, filed on Dec. 2, 2015, now Pat. No. 9,944,894.

(60) Provisional application No. 62/104,116, filed on Jan. 16, 2015.

(51) Int. Cl.
*C12N 5/00* (2006.01)
*C12N 5/0735* (2010.01)
*C12M 1/06* (2006.01)
*C12M 1/26* (2006.01)

(52) U.S. Cl.
CPC .......... *C12N 5/0606* (2013.01); *C12M 27/02* (2013.01); *C12M 33/22* (2013.01)

(58) Field of Classification Search
CPC ...... C12N 5/0606; C12M 27/02; C12M 33/22
See application file for complete search history.

(56) References Cited

U.S. PATENT DOCUMENTS

| 5,320,963 | A | * | 6/1994 | Knaack | B01D 21/0018 |
| | | | | | 210/615 |
| 6,190,913 | B1 | | 2/2001 | Singh | |
| 6,544,788 | B2 | | 4/2003 | Singh | |
| 8,445,273 | B2 | | 5/2013 | Green et al. | |
| 8,609,406 | B2 | | 12/2013 | Subramanian et al. | |
| 9,085,754 | B2 | | 7/2015 | Aberdam et al. | |
| 9,109,193 | B2 | | 8/2015 | Galliher et al. | |
| 2009/0029462 | A1 | | 1/2009 | Beardsley et al. | |
| 2010/0124781 | A1 | | 5/2010 | Nelson | |
| 2010/0136690 | A1 | | 6/2010 | Sundstroem et al. | |
| 2010/0144033 | A1 | | 6/2010 | Mandalam et al. | |
| 2011/0263016 | A1 | * | 10/2011 | Rancourt | C12N 5/0606 |
| | | | | | 435/366 |
| 2012/0207705 | A1 | | 8/2012 | Kara | |
| 2012/0225480 | A1 | | 9/2012 | Amit et al. | |
| 2013/0115695 | A1 | * | 5/2013 | Schulz | C12N 5/0606 |
| | | | | | 435/366 |
| 2013/0236961 | A1 | | 9/2013 | Amit et al. | |
| 2014/0099711 | A1 | | 4/2014 | Shimoni et al. | |
| 2014/0242693 | A1 | | 8/2014 | Fryer et al. | |

FOREIGN PATENT DOCUMENTS

| EP | 2155867 B1 | 5/2013 |
| EP | 2966163 A1 | 1/2016 |
| WO | 2011117821 A1 | 9/2011 |
| WO | 2012115686 A1 | 8/2012 |
| WO | 2013109520 A1 | 7/2013 |
| WO | 2015102528 A1 | 7/2015 |

OTHER PUBLICATIONS

Serra et al. "Improving expansion of pluripotent human embryonic stem cells in perfused bioreactors through oxygen control." J Biotechnol. Aug. 2, 2010;148(4):208-15.*

Wallman et al. "Biogrid—a microfluidic device for large-scale enzyme-free dissociation of stem cell aggregates." Lab Chip. Oct. 7, 2011;11(19):3241-8. . Epub Aug. 17, 2011.*

Moustafa et al. "Large area micropatterning of cells on polydimethylsiloxane surfaces." J Biol Eng. Oct. 24, 2014;8(1):24.*

Choo et al., "High-Level Production of a Monoclonal Antibody in Murine Myeloma Cells by Perfusion Culture Using a Gravity Settler", Biotechnology Progress, vol. 23, Issue 1, pp. 225-231, 2007.

Niebruegge et al., "Cardiomyocyte Production in Mass Suspension Culture: Embryonic Stem Cells as a Source for Great Amounts of Functional Cardiomyocytes", Tissue Engineering: Part A, vol. 14, Issue 10, pp. 1591-1601, 2008.

Shen et al., "CFD-aided cell settler design optimization and scale-up: Effect of geometric design and operational variables on separation performance", Biotechnology Progress, vol. 27, Issue 5, pp. 1282-1296, Sep.-Oct. 2011.

Kempf et al., "Controlling Expansion and Cardiomyogenic Differentiation of Human Pluripotent Stem Cells in Scalable Suspension Culture", Stem Cell Reports, vol. 3, Issue 6, pp. 1132-1146, Dec. 9, 2014.

Sylvia Niebrugge et al.,"Generation of Human Embryonic Stem Cell-Derived Mesoderm and Cardiac Cells Using Size-Specified Aggregates in an Oxygen-Controlled Bioreactor", Biotechnology and Bioengineering, vol. 102, No. 2, Feb. 1, 2009, Published online Jul. 25, 2008 in Wiley InterScience (www.interscience.wiley.com), 15Pages.

Celine Liu Bauwens et al."Control of Human Embryonic Stem Cell Colony and Aggregate Size Heterogeneity Influences Differentiation Trajectories", First published online in Stem cells express Jun. 26, 2008, www.StemCells.com, 11 Pages.

(Continued)

*Primary Examiner* — Titilayo Moloye
(74) *Attorney, Agent, or Firm* — GE Global Patent Operation; Pabitra Chakrabarti

(57) ABSTRACT

Provided herein are novel methods for expansion and passaging of cell aggregates comprising stem cells and/or differentiated cells and comprising the use of closed systems in stirred tank bioreactors. The methods of the invention permit closed system serial passage expansion of pluripotent stem cells and/or progeny thereof with associated pluripotency markers and differentiation potential.

14 Claims, 12 Drawing Sheets

(56) References Cited

OTHER PUBLICATIONS

Magnus Schroeder et al.,"Differentiation and Lineage Selection of Mouse Embryonic Stem Cells in a Stirred Bench Scale Bioreactor With Automated Process Control", Published online Sep. 27, 2005 in Wiley InterScience (www.interscience.wiley.com), 14 Pages.

Chi Zi et al., "Perfusion culture of hematopoietic cells in a stirred tank bioreactor", http://www.ncbi.nlm.nih.gov/pubmed/16176103, Jul. 2005;21(4):Abstract—2 Pages.

Akerstrom, "Expansion of Adherent Cells for Cell Therapy", Biology Education Centre, Uppsala University, and GE Healthcare Department of Cell Technologies, pp. 1-30, 2009.

Wallman et al., "Biogrid—a Microfluidic Device for Large-Scale Enzyme-Free Dissociation of Stem Cell Aggregates", The Royal Society of Chemistry, 'vol. No. 11, Issue No. 19, pp. 3241-3248, 2011.

Rowley et al., "Meeting Lot-Size Challenges of Manufacturing Adherent Cells for Therapy", BioProcess International, vol. No. 10, Issue No. 3, pp. 16-22, Mar. 2012.

Chen et al., "Scalable GMP Compliant Suspension Culture System for Human ES Cells", Stem Cell Research, vol. No. 8, Issue No. 3, pp. 388-402, May 2012.

Ting et al., "An Intermittent Rocking Platform for Integrated Expansion and Differentiation of Human Pluripotent Stem Cells to Cardiomyocytes in Suspended Microcarrier Cultures", Stem Cell Research, vol. No. 13, Issue No. 2, pp. 202-213, Sep. 2014.

Correia et al., "Combining Hypoxia and Bioreactor Hydrodynamics Boosts Induced Pluripotent Stem Cell Differentiation Towards Cardiomyocytes", Stem Cell Reviews and Reports, vol. No. 10, Issue No. 6, pp. 786-801, Dec. 2014.

"Cell Expansion", GE Healthcare Lifesciences, pp. 1-2, 2015, https://promo.gelifesciences.com/GL/XURI/expansion.html#.VL4A5keUf2k, Retrieved on Feb. 10, 2015.

Parmley, "Accelerating Stem Cells", BioCentury Publications, pp. 1-2, Sep. 24, 2015.

PCT Search Report and Written Opinion issued in connection with corresponding PCT Application No. PCT/EP2016/050707 dated Apr. 12, 2016.

Brian Michael Davis et al., Dec. 2, 2015, U.S. Appl. No. 14/956,408.

PCT Search Report and Written Opinion issued in connection with corresponding PCT Application No. PCT/EP2017/055892 dated Jun. 8, 2017.

* cited by examiner

PLURIPOTENT STEM CELL EXPANSION AND PASSAGE USING A STIRRED TANK BIOREACTOR

CROSS REFERENCE TO RELATED APPLICATIONS

This application is a Continuation-in-Part of U.S. non-provisional application Ser. No. 14/956,408 titled "Pluripotent Stem Cell Expansion and Passage using a Rocking Platform Bioreactor" filed Dec. 2, 2015, which claims priority to U.S. Provisional Application No. 62/104,116 titled "Pluripotent Stem Cell Expansion Using a Rocking Platform" filed Jan. 16, 2015, which applications are incorporated herein by reference in their entirety.

BACKGROUND

This disclosure relates generally to expansion and passaging of cells and/or cell aggregates using a stirred tank bioreactor.

A need for large scale pluripotent stem cell culture is emerging for applications in pluripotent stem cell banking (e.g., for induced pluripotent stem cells), commercial production of cells (e.g., GE's Cytiva™ cardiomyocytes), and cell expansion for clinical trials. Advances in feeder-free pluripotent stem cell culture have enabled large scale cell expansion in flasks, on microcarriers (150 to 250 microns in diameter) or on macrocarriers (~6 mm in diameter) in bioreactors. The use of suspension culture avoids some of the challenges that occur when culturing pluripotent cells on traditional microcarriers including inefficient seeding and release of cells from carriers, physical separation of microcarriers and cells during harvest, and formation of cell-carrier clumping that can lead to phenotypic changes in the cells. Typically, perfusion is used for suspension cultures in bioreactors.

However one challenge in perfusion/suspension culture is how to retain the cells in the bioreactor. Prior art provides some basic separation techniques-1) filtration, 2) gravity sedimentation, and 3) centrifugation. Filtration methods require some means to keep the filter from clogging over the required weeks of operation. A problem with gravity sedimentation is the varying sedimentation characteristics of different cells, the difficulty in scale-up to industrial systems, and difficulty in maintaining sterility. Similarly, centrifugation is routinely used in open cell culture but has found limited application in fully closed system cell culture due to concerns regarding sterility.

There is a need in the field for techniques which reduce human intervention and cross-contamination during the process of culturing cells, including pluripotent stem cells and/or differentiated human cells.

BRIEF DESCRIPTION

Described herein are improved methods for culturing cells, including pluripotent stem cells and/or differentiated human cells.

Provided herein are methods for expansion of cell aggregates in a closed system comprising
  a cell culture vessel;
  aggregate formation in the vessel;
  automated perfusion of cell aggregates in the vessel;
  gravity settling of cell aggregates during the perfusion; and
  aggregate harvest and passaging in the closed system.

Also provided herein are closed systems for use in expansion of cell aggregates using the methods described herein.

DRAWINGS

These and other features, aspects, and advantages of the present invention will become better understood when the following detailed description is read with reference to the accompanying drawings in which like characters represent like parts throughout the drawings, wherein.

Figure 8:
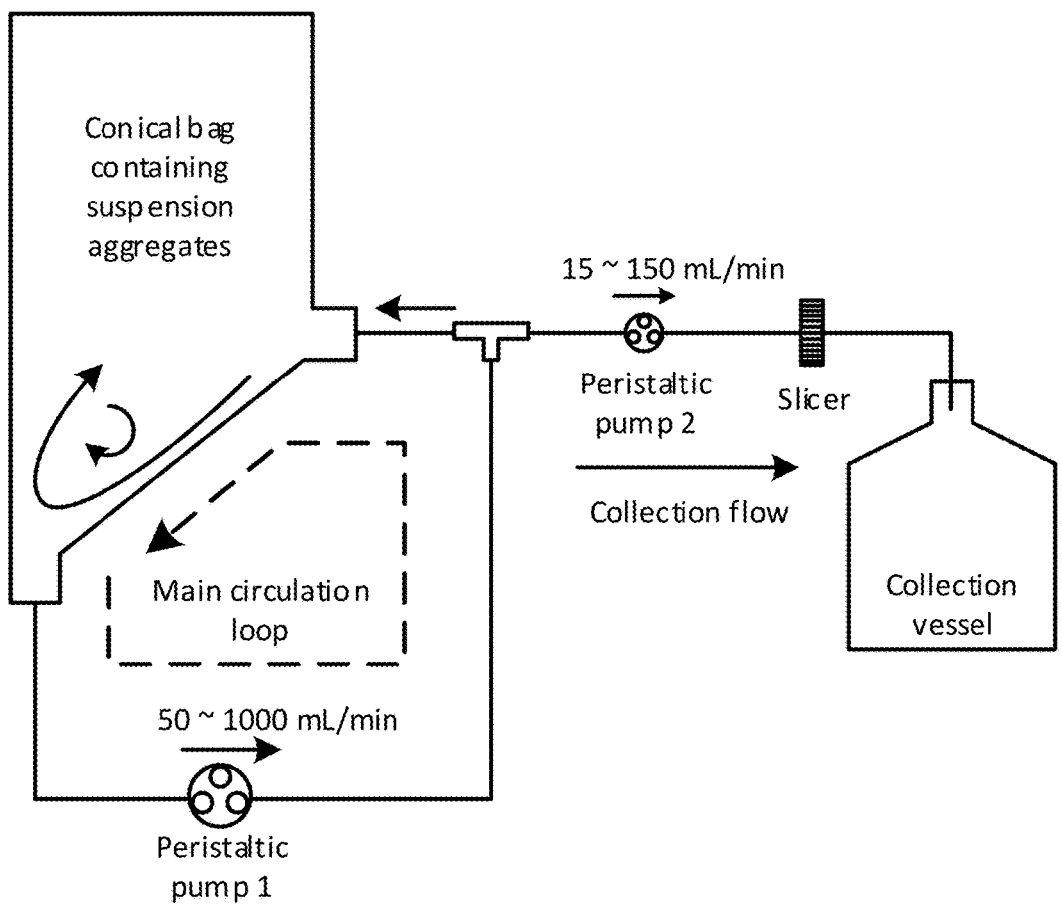

FIG. 8 shows a diagram of a method for closed system processing of aggregates through the slicer. A circulation loop driven by a pump and an in line conical bag suspends and distributes the aggregates. Tubing leading to the slicer is connected to the main circulation loop and a portion of the cell aggregates is delivered to the slicer through a second pump operating at a lower speed.

Figure 9B:
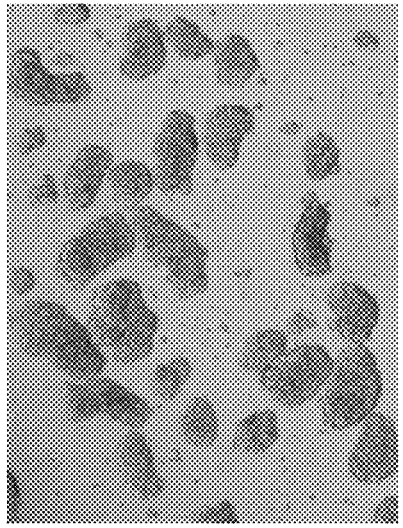
Figure 9A:
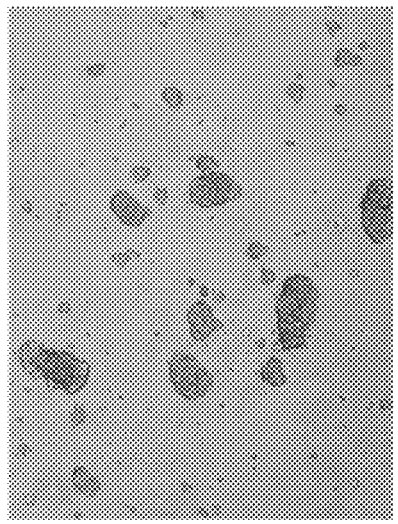
Figure 9C:
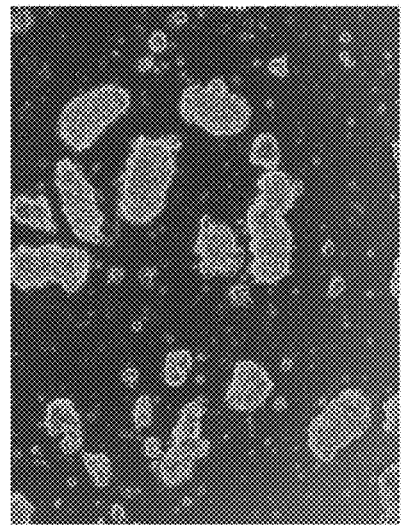

FIG. 9A, FIG. 9B and FIG. 9C shows images of the morphology of sliced aggregates of CT2 human embryonic stem cells.

Figure 10:
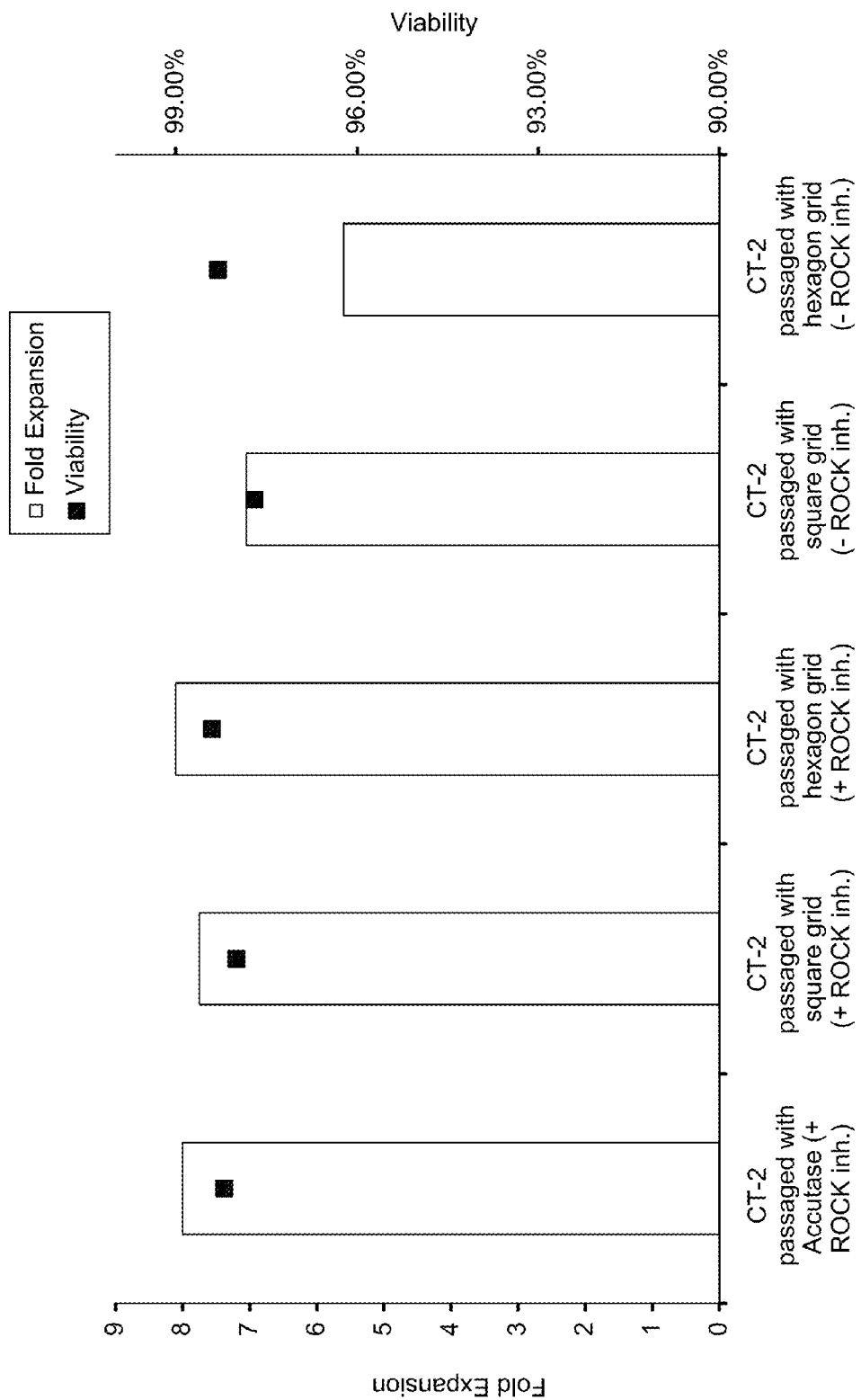

FIG. 10 shows expansion rate comparison after enzymatic passaging or mechanical passaging with the slicer on CT2 human embryonic stem cell aggregates seeded at 4×10^5 cells per mL.

Figure 11:
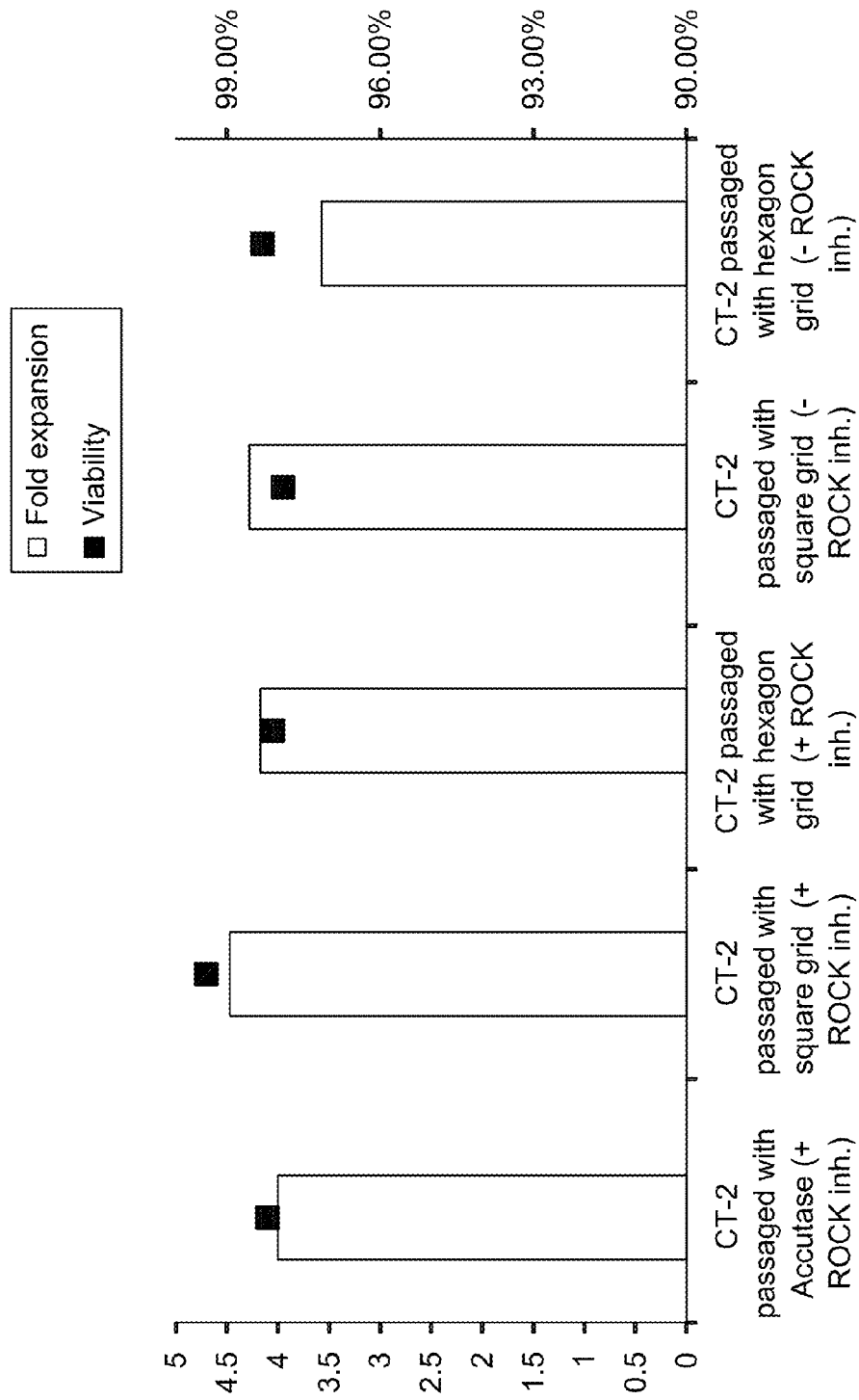

FIG. 11 shows expansion rate comparison after enzymatic passaging or mechanical passaging with the slicer on CT2 human embryonic stem cell aggregates seeded at 1.5×10^6 cells per mL. (1) CT-2 passaged with Accutase®+ROCK inhibitor; (2) CT-2 passaged with square grid+ROCK inhibitor; (3) CT-2 passaged with hexagon grid+ROCK inhibitor; (4) CT-2 passaged with square grid+ROCK inhibitor; (5) CT-2 passaged with hexagon grid+ROCK inhibitor.

Figure 12:
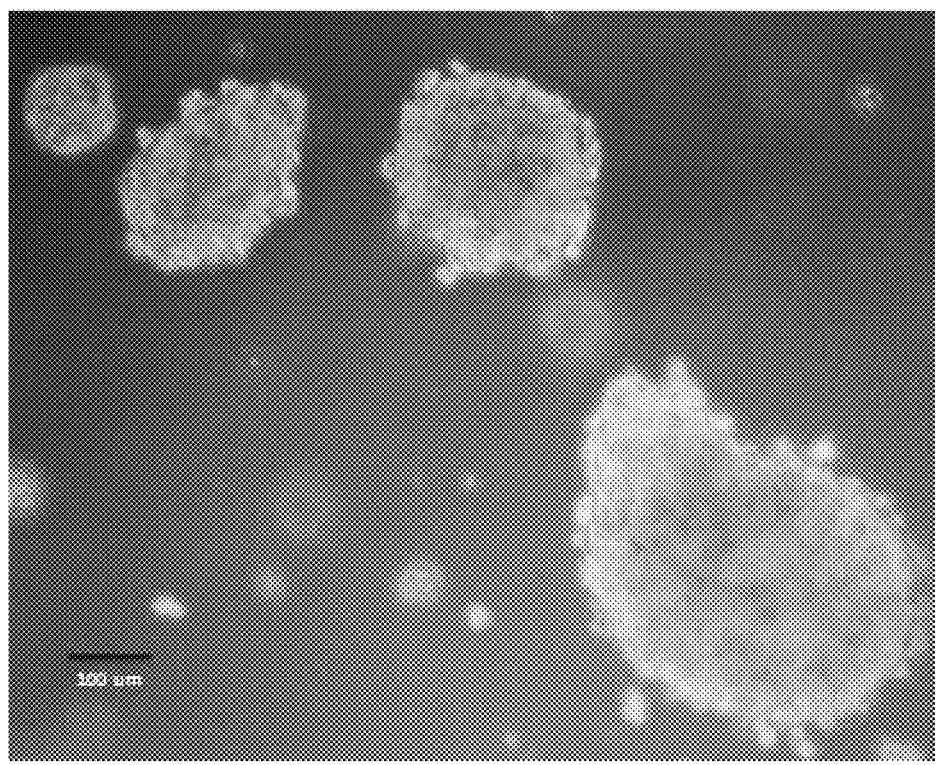

FIG. 12 shows CT2 human embryonic stem cell aggregate morphology in the stirred tank reactor.

DETAILED DESCRIPTION

"A" or "an" means herein one or more than one; at least one. Where the plural form is used herein, it generally includes the singular.

As used herein "perfusion" refers to the process of keeping culture cells alive by continuously feeding the cells with fresh media and removing spent media while keeping cells in culture.

"Aggregate" refers to an association of cells in which the association is caused by cell-cell interaction rather than adherence to a substrate. In an aggregate, two or more cells associate with each other by biologic attachments to one another. This can be through surface proteins, such as extracellular matrix proteins. In one embodiment, cells can be initially grown on a substrate where some cells associate with (adhere to) the substrate but further growth forms cell-cell associations (aggregation) that do not depend on association (adherence) of the further-grown cells with the substrate. In another embodiment, cells spontaneously associate in suspension to form cell-cell attachments independent of any adherence to a surface. A cellular feeder layer is also considered a substrate. So attachment of cells to a feeder layer is also a form of adherent culture (not an aggregate) since attachment of the cells is not to each other but to the cells in the feeder layer.

"Expansion" refers to the proliferation of cells with or without differentiation and may include no passaging, one passage or more than one passage and/or serial passages. In one embodiment, expansion refers to proliferation of cells without differentiation and includes one or more than one passage and/or serial passages.

"Stem cell" means a cell that can undergo self-renewal (i.e., progeny with the same differentiation potential) and also produce progeny cells that are more restricted in differentiation potential. Within the context of the disclosure, a stem cell would also encompass a more differentiated cell that has de-differentiated, for example, by nuclear transfer, by fusion with a more primitive stem cell, by introduction of specific transcription factors, or by culture under specific conditions. A "pluripotent stem cell" can potentially produce any cell or tissue the body needs to repair itself. Pluripotent stem cells are also able to self-renew, and can perpetually create more copies of themselves. Pluripotent stem cells include induced pluripotent stem cells (iPSCs) and embryonic stem cells (ESCs).

"Culture vessel" includes disposable and non-disposable plasticware, bags and/or containers and/or bioreactors. The term includes single-use plasticware, bags and/or containers and/or bioreactors and multiple-use plasticware, bags and/or containers and/or bioreactors.

"Closed system" refers to a culture vessel and accessory components that have been pre-sterilized while closed and/or sealed and retains integrity and/or sterility. The vessels and components are utilized without breach of the integrity of the system, permit fluid transfers in and/or out while maintaining asepsis, and are connectable to other closed systems without loss of integrity. A closed system bioreactor and/or vessel refers to a system in which cells, cell culture medium, chemicals and reagents are aseptically added, removed and/or manipulated without breach of integrity of the system (e.g., by opening the cap of a tube or lifting the lid off a cell culture plate or dish). Single-use or multiple-use bags and/or containers and/or bioreactors in a closed system are added onto or into the closed system for example by sterile tube welding at the site of the vessel or bioreactor.

A "subject" is a vertebrate, preferably a mammal, more preferably a human. Mammals include, but are not limited to, humans, farm animals, sport animals, and pets. Subjects in need of treatment by methods of the present invention include those suffering from a loss of function as a result of physical or disease-related damage.

The term "therapeutically effective amount" refers to the amount determined to produce any therapeutic response in a mammal. For example, effective amounts of the therapeutic cells or cell-associated agents may prolong the survivability of the patients. Alternatively, said treatment may be prophylactic and prevent and/or inhibit overt clinical symptoms. Treatments that are therapeutically effective within the meaning of the term as used herein, include treatments that improve a subject's quality of life even if they do not improve the disease outcome per se. Such therapeutically effective amounts are ascertained by one of ordinary skill in the art through routine application to subject populations such as in clinical and pre-clinical trials. Thus, to "treat" means to deliver such an amount.

"Treat," "treating" or "treatment" are used broadly in relation to the invention and each such term encompasses, among others, ameliorating, inhibiting, or curing a deficiency, dysfunction, disease, or other deleterious process, including those that interfere with and/or result from a therapy.

Large scale pluripotent stem cell culture is needed for pluripotent stem cell banking (e.g., for induced pluripotent stem cells), commercial production of cells (e.g., GE's Cytiva™ cardiomyocytes), and/or cell expansion for clinical trials. Pluritpotent stem cells may be induced pluripotent cell (iPS cells), "true" embryonic stem cell (ES cells) derived from embryos, embryonic stem cells made by somatic cell nuclear transfer (ntES cells), or embryonic stem cells from unfertilized eggs (parthenogenesis embryonic stem cells, or pES cells). Large scale cell feeder-free embryonic stem cell expansion in flasks is labor intensive, space prohibitive and separated populations may exhibit phenotypic drift. Therefore, there have been attempts in the field for developing alternative approaches for large scale pluripotent stem cell culture; e.g., CellSTACK® (Corning), Cell Factory (Nunc®) and bioreactors (microcarriers or suspension culture).

There are many types of bioreactors used for cell culture, including but not limited to stirred tank reactors, spinner flasks, orbital shakers, rocking motion, and paddle wheel. Those skilled in the art will recognize that there are also alternative approaches for cell culture in bioreactors.

Suspension aggregate culture of pluripotent stem cells in an impeller stirred tank bioreactor system has been demonstrated (Chen, V C et. al, *Stem Cell Res.* 2012 May; 8(3):388-402) which obviates the need for any substrate or carriers in the bioreactor culture. In the Chen method for passaging cells from suspension culture, aggregates were harvested by centrifugation. By contrast, the methods provided herein allow for closed system expansion (including seed, perfusion, passage and harvest) of pluripotent stem cells and/or pluripotent stem cell aggregates in a closed system using a stirred tank bioreactor. Further, the methods described herein also allow for suspension and/or non-adherent cultures of pluripotent stem cells in closed systems without the use of membrane filters and/or centrifugation and/or enzyme digestion, which allows for maintenance of sterility in closed systems, reduces costs (e.g., for setting up centrifuges) and also reduces human intervention which assists in reducing cross contamination. Also contemplated within the scope of embodiments presented herein is the use of the present methods in combination with additional passages of the cells or cell aggregates which may include the use of membrane filters and/or centrifugation and the like and may include the use of enzyme digestion for dissociation of aggregates in the additional passages of the cells or cell aggregates.

Previously described methods for expansion of pluripotent stem cells in stirred tank bioreactors (e.g., Niebruegge et al., *Tissue Engineering*: Part A, 2008, Volume 14, Issue 10, Pages 1591-1601) disclose expansion of mouse stem cells. Further such previously described methods are focused on sustaining the stem cell culture for a sufficient length of time and, generally, consequential differentiation of the stem cells. By contrast, the methods described herein allow for expansion of human stem cells, followed by dissociation of aggregates and passaging of the disassociated cells so that the cells retain their pluripotency through expansion and serial passages. In addition, the methods of expansion and passage described herein are carried out in a closed system which ensures sterility during the production process. Typically, previously described stem cell expansion methods employ Rho-associated protein kinase inhibitors (ROCK inhibitors) for sustaining the cell culture during enzymatic passaging. A drawback of employing ROCK inhibitors for stem cell expansion and passage is that the ROCK inhibitors affect chromosomal stability, possibly triggering karyotypic abnormalities and genetic drift of the stem cells. By contrast, the expansion and passaging of stem cells described herein is carried out in the absence of ROCK inhibitors thereby reducing karyotypic abnormalities and genetic drift and allowing for retention of pluripotency during the passaging of the stem cells.

The methods described herein rely on gravity settling combined with automated perfusion in closed systems. Additionally, in some embodiments, the methods described herein comprise the use of a slicer thereby allowing for enzyme free dissociation of cell aggregates between successive passages of cells. Certain previously described lamellar gravity settlers require the cells or cell aggregates to roll down inclined planes/tubes. The drawbacks of such lamellar gravity settlers for suspension aggregate applications include: the cell aggregates are subject to shear stress which reduces the efficiency of the expansion process, the large cell loss due to incomplete settling efficiency, and aggregate association/adherence to the gravity settler. Lamellar gravity settlers have been used to separate and discard cell aggregates from the cell population. By contrast, the methods described herein separate and discard the single cells (low viability stem cells) while retaining aggregates for subsequent passaging.

Other previously described methods for medium exchange temporarily pause agitation, thereby allowing aggregates to gravity settle in the stirred tank bioreactor. After the aggregates settle, a portion of the spent medium can be removed from the bioreactor and replaced with fresh medium. A risk of this approach is the potential for aggregate conglomeration while the aggregates are concentrated together at the bottom surface.

Accordingly, described herein are methods for cell aggregate expansion, including human pluripotent stem cell expansion, in stirred tank bioreactors. The continuous or discontinuous stirring of the culture fluid provides mixing and aeration, resulting in a robust environment for cell growth. The method employs culture vessels of varying sizes, providing ease of operation and protection against cross-contamination. Sensors are available for continuous monitoring of dissolved oxygen, pH and medium components such as lactate and glucose, with real time controls and data storage. The platform software provides the ability to perform continuous or discontinuous perfusion/medium exchange in a closed system.

Typically, during perfusion, there are different ways to keep the cells in culture while removing spent media. One way is to keep the cells in the bioreactor by using capillary fibers or membranes with pore sizes smaller than the size of the cell. Another method is to utilize a "lily pad" floating filter that keeps the cells in the bioreactor while allowing the media to be removed. Another method is the use of a centrifuge to separate cells and return them to the bioreactor. Yet another method uses a physical approach such as acoustics to trap cells in the cell culture vessel or associated tubing while spent medium is removed.

By contrast, the methods described herein rely on gravity settling of cell aggregates which allows for removal of spent media without the use of filtration systems which are typically used to keep the cells in the bioreactor while concomitantly allowing the media to be removed. An advantage to this method is the loss of single cells, which are predominantly non-viable in pluripotent stem cell cultures, and maintenance of aggregates, thereby increasing the overall quality and viability of the culture.

By continuously removing spent media and replacing it with new media, nutrient levels are maintained for optimal growing conditions and cell waste product is removed to avoid toxicity. When perfusion is carried out in a closed system using the methods described herein, the possibility of contamination is reduced. Advantageously, the closed systems and cell culture methods described herein utilize gravity-settling of cell aggregates thereby allowing for membrane-less perfusion which allows for reduction in losses due to adhesion of cells to filtration membranes and/or damage to cells due to shear during the filtration process.

The methods described herein are preferably employed in closed systems to minimize risk of culture contamination and cell cross-contamination and allow for reaching high viabilities and high cell densities with confidence. The methods described herein are designed for ease-of-use and reliability.

Provided herein are methods which describe pluripotent stem cell expansion as suspension aggregates in a stirred tank system, with serial passage. Also provided herein are examples showing that the use of a stirred tank reactor in combination with a slicer for passaging is advantageous for expansion and serial passage of pluripotent stem cells in a unified closed system, specifically in reductions of time, reagents and labor.

Also provided herein is a specific assembly of tubing connected to culture vessel (e.g., a stirred tank bioreactor) that interacts with computer controlled peristaltic pumps to drive automated medium exchange. In one embodiment, the tubing is shaped like a T, with a lower vertical piece of tubing, a branch point, and two additional lengths of tubing connected at the branch point. The additional tubing is placed onto peristaltic pumps that are controlled by software. A slow harvest rate is used to draw off medium. The vertical nature of the tubing allows aggregates to gravity settle at rates that exceed the flow rate of the removed medium. The net effect is that aggregates remain in the optimal cell culture conditions in the vessel (e.g., a stirred tank bioreactor) during the medium removal step. Medium removal can be continuous e.g., for up to 8 hours, up to 4 hours, and the like, but medium removal can be performed for much shorter or longer lengths of time. Following the medium removal step, fresh medium is rapidly added to the vessel (e.g., the stirred tank bioreactor) over seconds to a few minutes or over any suitable length of time. The cycle of medium removal/rapid medium addition is repeated for the desired length of cell culture. In alternate instances, perfusion may be discontinuous and such embodiments are also contemplated within the scope of embodiments presented herein.

The automated perfusion design described herein is inherently low cost, is fully compatible with culture vessels including stirred tank reactors, can be adjusted to be fully compatible with any other culture vessel, and does not require any filters which would add cost and increase the risk for fouling and reduce performance. Further the automated perfusion described herein does not comprise moving parts or electronics which would increase complexity, cost, and risk for failure.

Provided herein is a method for expansion of cell aggregates in a closed system comprising
providing a cell culture vessel;
aggregate formation in the vessel;
automated perfusion of cell aggregates in the vessel;
gravity settling of cell aggregates during the perfusion; and
aggregate harvest and passaging in the closed system.

In some embodiments, the passaging in the closed system is carried out in the presence of a Rho-associated protein kinase (ROCK) inhibitor (e.g., a concentration of the ROCK inhibitor in the cell culture medium in the vessel is about 10 micromolar). In other embodiments of the method described above, the passaging in the closed system is carried out substantially in the absence of an agent which maintains the viability of passaged, monodispersed or disaggregated pluripotent cells. In some of such embodiments, the agent which maintains the viability of pluripotent cells is a Rho-associated protein kinase (ROCK) inhibitor. In some embodiments of the method described above, the passaging in the closed system is carried out in the absence of a ROCK inhibitor. In some of such embodiments, the ROCK inhibitor is Y27632. As used herein, in one embodiment, "substantially in the absence of an agent which maintains the viability of passaged, monodispersed or disaggregated pluripotent cells" means there is no agent added to the cell culture medium to maintain the viability of passaged, monodispersed or disaggregated pluripotent cells. In another embodiment, "substantially in the absence of an agent which maintains the viability of passaged, monodispersed or disaggregated pluripotent cells" means that the concentration of the agent in the cell culture medium present in the vessel is less than 1 micromolar, or less than 5 micromolar or less than 10 micromolar.

In some embodiments, the cell aggregates which are expanded are of plant, animal, insect or microbial origin. In some embodiments, the cell aggregates which are expanded comprise human pluripotent stem cells or differentiated human cells or a combination thereof. In some embodiments, the cell aggregates which are expanded comprise human pluripotent stem cells.

In some embodiments, the cell culture vessel is a stirred tank bioreactor. In some embodiments, said automated perfusion is carried out in the closed system without human intervention.

In some embodiments, the gravity settling chamber is at least 1 cm in length and positioned in an orientation that drives gravity settling of cell aggregates.

In some embodiments, the automated perfusion is conducted at a rate that allows gravity settling of cell aggregates of about 100 micron to about 800 micron diameter.

In some embodiments, the methods described above further comprise one or more additional expansions of the cell aggregates and/or progeny thereof by conducting serial passages. In some of such embodiments, the one or more of the additional expansions of the cell aggregates and/or progeny thereof, are carried out by passaging into a second vessel having a membrane filter.

In some embodiments, the methods described above comprise one or more additional expansions of the cell aggregates and/or progeny thereof where the one or more additional passages are conducted in the same vessel. In other embodiments, the methods described above comprise one or more additional expansions of the cell aggregates and/or progeny thereof where the one or more additional passages are conducted in a second vessel in the absence of a membrane filter (e.g., by gravity settling of cell aggregates) in the culture vessel. In other instances, the methods described above comprise one or more additional expansions of the cell aggregates and/or progeny thereof where the one or more additional passages are conducted in a second vessel having a membrane filter (e.g., a floating membrane filter).

In such embodiments, the additional expansions and/or passages may be carried out in any order. By way of example, an initial passage may be carried out under membrane-free conditions (e.g., by gravity settling of cell aggregates) in the culture vessel, followed by one or more additional expansions carried out in a culture vessel having a membrane filter. As an alternate example, one or more initial expansions and/or passages may be carried out in culture vessels which comprise membrane filters, followed by subsequent expansions and/or passages under membrane-free filtration conditions (e.g., by gravity settling of cell aggregates). Accordingly any sequence of expansions and/or passages comprising membrane-filtration or membrane-free filtration is contemplated within the scope of embodiments described herein where said sequence includes at least one expansion under the present membrane-free conditions (e.g., by gravity settling of cell aggregates).

In some embodiments, serial passaging of cell aggregates is enabled by enzyme-free passaging using slicer grids in the closed system. In some of such embodiments, the cell aggregates are dissociated with a slicer grid having blades separated by a distance of about 20 to about 500 microns. In some other embodiments, the cell aggregates are dissociated with a slicer grid having blades separated by a distance of about 100 microns. In some of such embodiments, the cell aggregates are dissociated with a slicer grid in line with tubing and a device for mixing of cell aggregates. In other words, in some embodiments, the cell aggregates are mixed in e.g., a conical bag, shown in FIG. 8, prior to dissociation with a slicer and the mixing bag is typically placed between the culture vessel and the slicer in the closed system.

Figure 5:
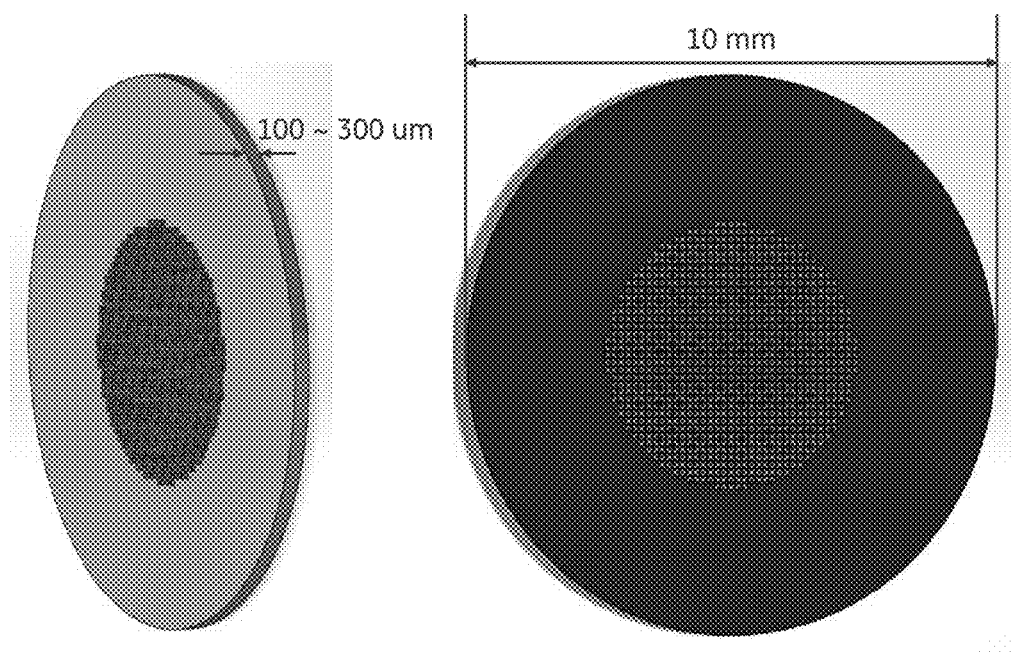
FIG. 5 shows a diagram of the 10 mm slicer grid structure with thickness of 100 um to 300 um.
Figure 6:
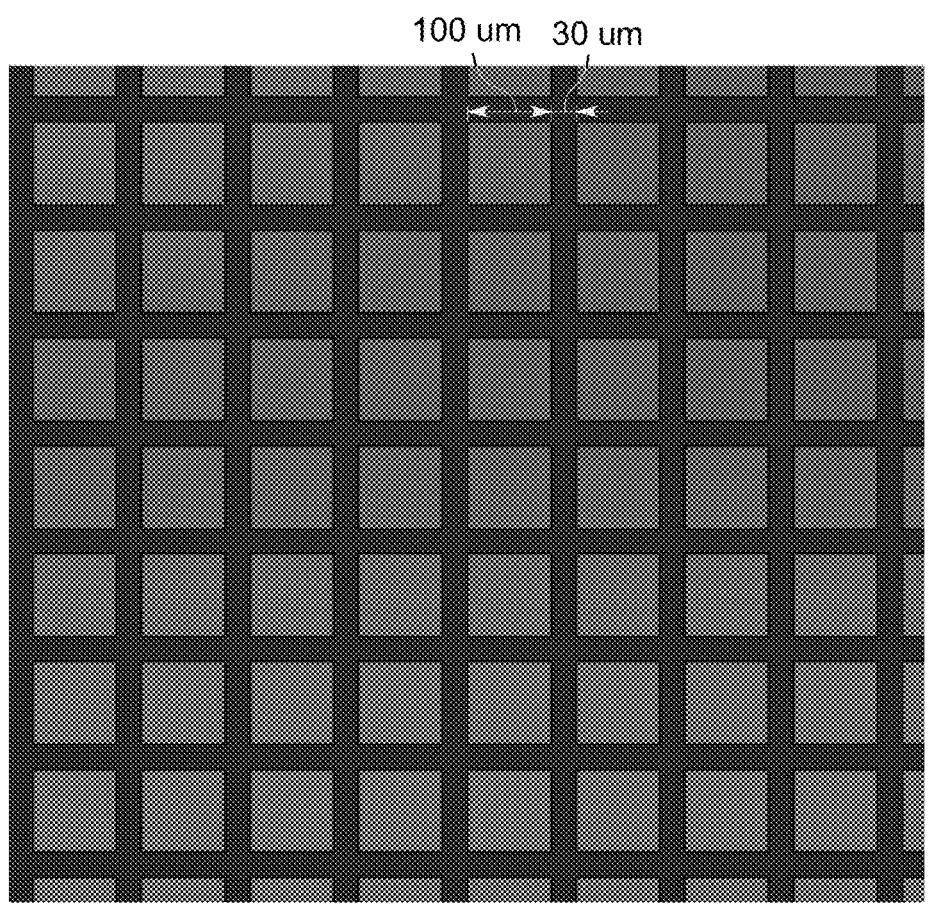
FIG. 6 shows a diagram of the square grid slicer with 100 um spacing between walls and 30 um wall thickness.
Figure 7:
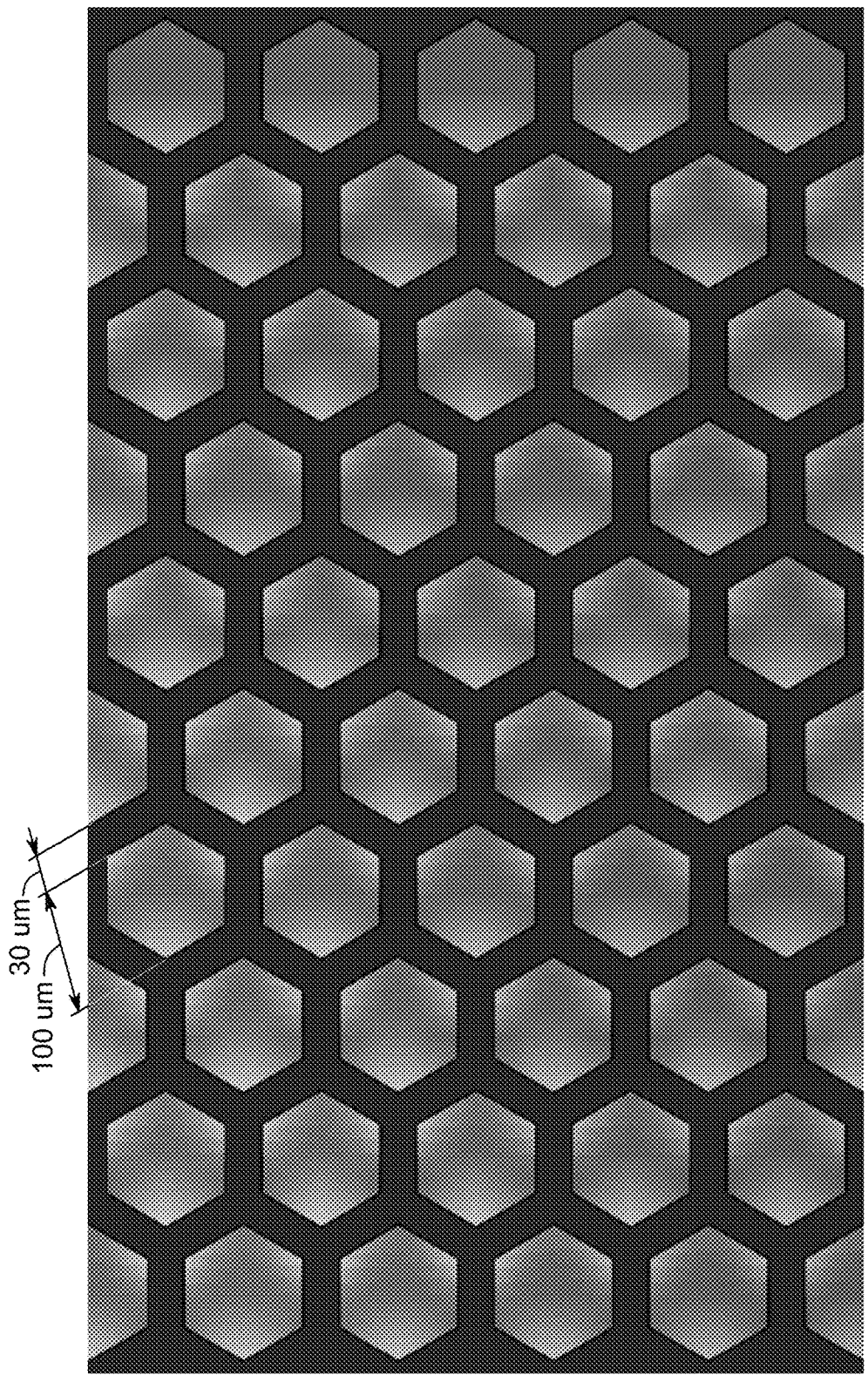
FIG. 7 shows a diagram of the hexagon grid slicer with 100 um spacing between walls and 30 um wall thickness.

The cell aggregate concentration used to pass through the slicer influences the recovery of sliced cell aggregates at high viability. Unexpectedly, it was found that slicing of cell aggregate concentrations below about $3 \times 10^6$ cells per mL produced higher viability samples with higher recovery than cell concentrations greater than about $3 \times 10^6$ cells per mL using a slicer geometry shown in FIGS. 5-7. Those skilled in the art will recognize that alternative slicer geometries will modify the threshold concentration that provides relatively higher viability and recovery. Fouling was minimized by maintaining a uniform suspension of aggregates in the flow stream, for example by using the mixing device shown in FIG. 8, resulting in higher cell viability and recovery. Advantageously, the use of a slicer obviates the need for the Y27632 ROCK inhibitor during expansion of sliced pluripotent stem cell aggregates, unlike enzymatically passaged pluripotent stem cell aggregates which generally requires agents such as the Y27632 ROCK inhibitor to maintain the viability of single pluripotent cells.

In one group of embodiments the slicer is coated with a hydrophobic material. In some embodiments, the slicer comprises a hydrophobic material.

Also contemplated are certain other embodiments, wherein serial passaging of the cell aggregates is enabled by disassociation of the cell aggregates in the closed system vessel in the presence of an enzyme. In such embodiments, additional expansion or passaging may be carried out in the presence of a ROCK inhibitor.

In some embodiments of the methods described above, during the expansions and/or passages, the average diameter of each expanded cell aggregate is no more than about 800 micron in size. In some embodiments of the methods described above, during the expansions and/or passages, the average diameter of each expanded cell aggregate is no more than about 500 micron in size. In some embodiments of the methods described above, during the expansions and/or passages, the average diameter of each expanded cell aggregate is no more than about 400 micron in size. In some embodiments of the methods described above, during the expansions and/or passages, the average diameter of each expanded cell aggregate is no more than about 300 micron in size.

In some embodiments, the volume of the culture vessel is from about 50 mL to about 100 L. In some embodiments, the volume of the culture vessel is from about 50 mL to about 50 L. In some embodiments, the volume of the culture vessel is from about 100 mL to about 10 L. In some embodiments, the volume of the culture vessel is from about 100 mL to about 5 L. In some embodiments, the volume of the culture vessel is from about 150 mL to about 1 L. In some embodiments, the volume of the culture vessel is from about 50 mL to about 20 L. In some embodiments, the volume of the culture vessel is from about 200 mL to about 2 L or greater than 2 L.

Further provided herein is a method for passaging cell aggregates wherein cell aggregates are reduced in size by a slicer grid associated with a bioreactor in a closed system. In one group of embodiments for any method described herein, the cell aggregates are passaged in volumes exceeding 100 mL. In other words, passaging has generally been carried out in smaller volumes of culture medium and with lower cell counts. By contrast, the present methods allow for use of large volumes of culture medium in closed systems thereby allowing for passaging of cell aggregates in bioreactors and/or on industrial scale. The use of a slicer grid in combination with a bioreactor in a closed system for cell aggregate passaging in large volumes e.g., exceeding 100 mL has not been disclosed in the art prior to this disclosure. In another embodiment, the cell aggregates are passaged in volumes exceeding 250 mL, 500 mL, 1 L, 2 L or 5 L. In one embodiment, the slicer grid is a polygonal slicer grid. In one instance, said passaging of cell aggregates in volumes exceeding 100 mL is performed without the addition of a ROCK inhibitor (e.g., Y27632) to the medium.

In some embodiments of the method for passaging cells described above, the cell aggregates are dissociated with a slicer grid having blades separated by a distance of about 20 to about 500 microns. In some embodiments of the method for passaging cells described above, the cell aggregates are dissociated with a slicer grid having blades separated by a distance of about 100 microns. In some of such embodiments, the cell aggregates are dissociated with a slicer grid in line with tubing and a device for mixing of cell aggregates. In certain instances, the slicer is coated with a hydrophobic material. In other instances, the slicer comprises a hydrophobic material.

In some embodiments of the method for passaging cells described above, the average diameter of each cell aggregate prior to passaging is no more than about 800 micron in size. In some embodiments of the method for passaging cells described above, the average diameter of each cell aggregate prior to passaging is no more than about 500 micron in size. In some embodiments of the method for passaging cells described above, the average diameter of each cell aggregate prior to passaging is no more than about 400 micron in size. In some embodiments of the method for passaging cells described above, the average diameter of each cell aggregate prior to passaging is no more than about 300 micron in size.

In another aspect, provided herein is a method for expansion of cell aggregates in a closed system comprising
providing a stirred tank bioreactor vessel;
aggregate formation in the vessel;
automated perfusion of cell aggregates in the vessel;
gravity settling of cell aggregates during the perfusion;
aggregate harvesting and enzyme-free slicing of cell aggregates; and
passaging in the closed system.

In some embodiments of the method described above, the passaging in the closed system is carried out in the presence of a ROCK inhibitor (e.g., a concentration of the ROCK inhibitor in the cell culture medium in the vessel is about 10 micromolar). In other embodiments of the method described above, the passaging in the closed system is carried out substantially in the absence of an agent which maintains the viability of passaged, monodispersed or disaggregated pluripotent cells. In some of such embodiments, the agent which maintains the viability of pluripotent cells is a Rho-associated protein kinase (ROCK) inhibitor. In some embodiments of the method described above, the passaging in the closed system is carried out in the absence of a ROCK inhibitor. In some of such embodiments, the ROCK inhibitor is Y27632. As used herein, in one embodiment, "substantially in the absence of an agent which maintains the viability of passaged, monodispersed or disaggregated pluripotent cells" means there is no agent added to the cell culture medium to maintain the viability of passaged, monodispersed or disaggregated pluripotent cells. In another embodiment, "substantially in the absence of an agent which maintains the viability of passaged, monodispersed or disaggregated pluripotent cells" means that the concentration of the agent in the cell culture medium present in the vessel is less than 1 micromolar, or less than 5 micromolar or less than 10 micromolar Accordingly, the methods provided herein enable several workflows including and not limited to (1) Aggregate formation in bioreactors including from these sources: enzymatically dissociated aggregates (e.g., Accutase™), cryopreserved stocks, and/or mechanically sliced aggregates (e.g., polygonal slicer grid); (2) Expansion method in stirred systems: non-perfusion bioreactor with tubing assembly for gravity settling, and/or perfusion bioreactor; and (3) Serial Passaging: enzyme added to aggregates in cell culture vessel (e.g., Accutase™ in bioreactor), enzyme added to aggregates outside of cell culture vessel and/or mechanical passage using polygonal slicer grid.

Further, the methods described herein are suitable for use in a variety of bioreactors that have been used for suspension culture of cells including and not limited to stirred suspension bioreactors, rocking motion bioreactors, spinner flasks, orbital motion bioreactors, rotary motion bioreactors, and tangential fluid flow bioreactors. The methods described herein, including filter free gravity settling for perfusion and enzymatic-free passaging using a slicer, are compatible with all such bioreactor systems and enable closed system aggregate formation, perfusion, expansion, harvest and passaging in such bioreactors.

Contemplated within the scope of embodiments provided herein is the use of the methods described herein for generating banks of cells, for generating expanded cell aggregates for research applications, for therapeutic and/or diagnostic testing (e.g., drug testing, toxicology or quality control assays in clinical trials), and/or for treatment of patients. Provided herein are methods comprising administering to subjects in need thereof a pharmaceutical composition comprising a pharmaceutically-acceptable carrier and at least one cell and/or cell aggregate obtained from the methods described herein.

Also provided herein is a method of treating a disorder in a subject in need of treatment by administering a therapeutically effective amount of the cells and/or aggregates produced in the methods above to the subject in need thereof. The methods further include a method of treating a disorder in a subject in need of treatment by administering a therapeutically effective amount of a pharmaceutical composition comprising a pharmaceutically-acceptable carrier and the cells and/or aggregates produced in the methods above. It will be understood that the methods described herein are applicable to pluripotent stem cells and also differentiated cells.

In some embodiments the purity and/or homogeneity of the expanded cells obtained from the methods described herein and/or for administration to a subject is about 100% (substantially homogeneous). In other embodiments the purity and/or homogeneity of the expanded cells obtained from the methods described herein and/or for administration to a subject is 95% to 100%. In some embodiments the purity and/or homogeneity of the expanded cells obtained from the methods described herein and/or for administration to a subject is 85% to 95%. In the case of admixtures with other cells, the percentage can be about 10%-15%, 15%-20%, 20%-25%, 25%-30%, 30%-35%, 35%-40%, 40%-45%, 45%-50%, 60%-70%, 70%-80%, 80%-90%, or 90%-95%.

The choice of formulation for administering the cells for a given application will depend on a variety of factors. Prominent among these will be the species of subject, the nature of the condition being treated, its state and distribution in the subject, the nature of other therapies and agents that are being administered, the optimum route for administration, survivability via the route, the dosing regimen, and other factors that will be apparent to those skilled in the art. For instance, the choice of suitable carriers and other additives will depend on the exact route of administration and the nature of the particular dosage form Final formulations of the aqueous suspension of cells/medium will typically involve adjusting the ionic strength of the suspension to isotonicity (i.e., about 0.1 to 0.2) and to physiological pH (i.e., about pH 6.8 to 7.5). The final formulation will also typically contain a fluid lubricant.

In some embodiments, cells are formulated in a unit dosage injectable form, such as a solution, suspension, or emulsion. Pharmaceutical formulations suitable for injection of cells typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof. The skilled artisan can readily determine the amount of cells and optional additives, vehicles, and/or carrier in compositions to be administered in methods of the invention.

Compositions can be administered in dosages and by techniques well known to those skilled in the medical and veterinary arts taking into consideration such factors as the age, sex, weight, and condition of the particular patient, and the formulation that will be administered (e.g., solid vs. liquid).

It is to be appreciated that a single dose may be delivered all at once, fractionally, or continuously over a period of time. The entire dose also may be delivered to a single location or spread fractionally over several locations.

In various embodiments, cells may be administered in an initial dose, and thereafter maintained by further administration. Cells may be administered by one method initially, and thereafter administered by the same method or one or more different methods. The levels can be maintained by the ongoing administration of the cells. Various embodiments administer the cells either initially or to maintain their level in the subject or both by intravenous injection. In a variety of embodiments, other forms of administration are used, dependent upon the patient's condition and other factors, discussed elsewhere herein. Suitable regimens for initial administration and further doses or for sequential administrations may all be the same or may be variable. Appropriate regimens can be ascertained by the skilled artisan, from this disclosure, the documents cited herein, and the knowledge in the art. The dose, frequency, and duration of treatment will depend on many factors, including the nature of the disease, the subject, and other therapies that may be co-administered. In any of the embodiments described herein, the cells may be differentiated or non-differentiated. In any of the embodiments described herein, the cells may be dissociated or aggregates. In any of the embodiments described herein the cells and/or cell aggregates may comprise a combination of pluripotent stem cells and progeny thereof.

EXAMPLES

Material and Methods

Figure 1:
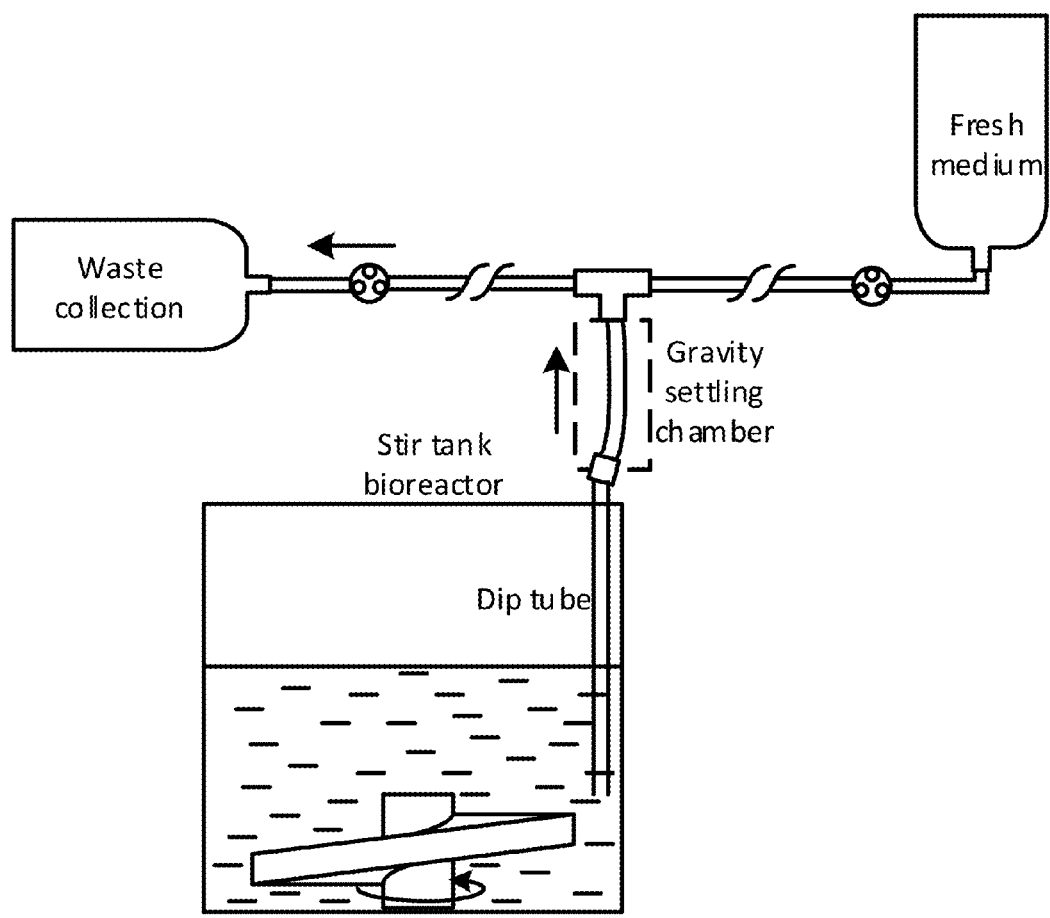
FIG. 1 shows a diagram of the tubing assembly for gravity settling and medium exchange in stirred tank bioreactors in which spent medium is being removed from the bioreactor in a vertical orientation.
Figure 2:
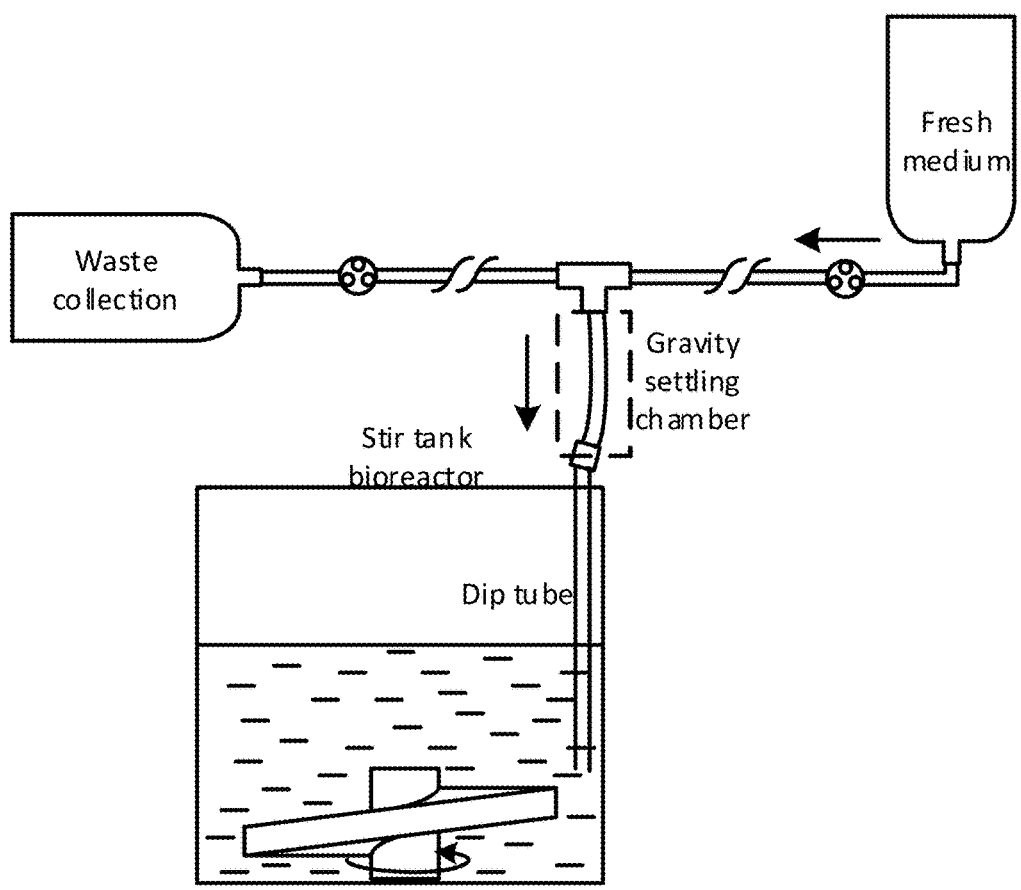
FIG. 2 shows a diagram of the tubing assembly for gravity settling and medium exchange in stirred tank bioreactors in which fresh medium is being added to the bioreactor in a vertical orientation.
Figure 3:
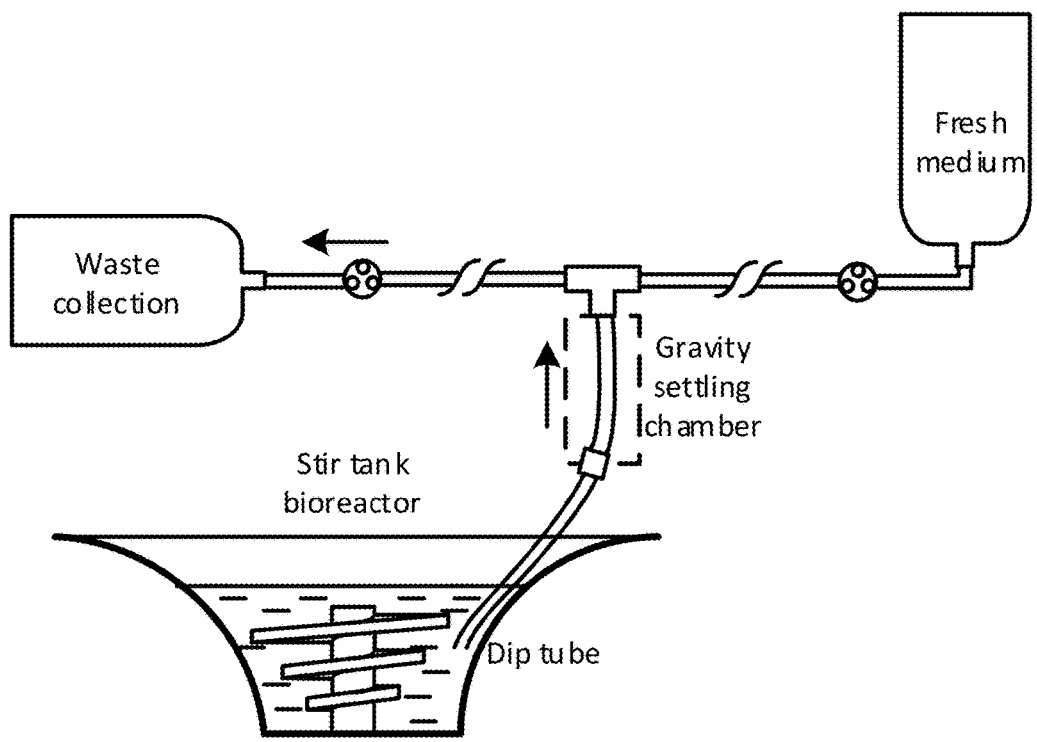
FIG. 3 shows a diagram of the tubing assembly for gravity settling and medium exchange in stirred tank bioreactors in which spent medium is being removed from the bioreactor in a slanted orientation.
Figure 4:
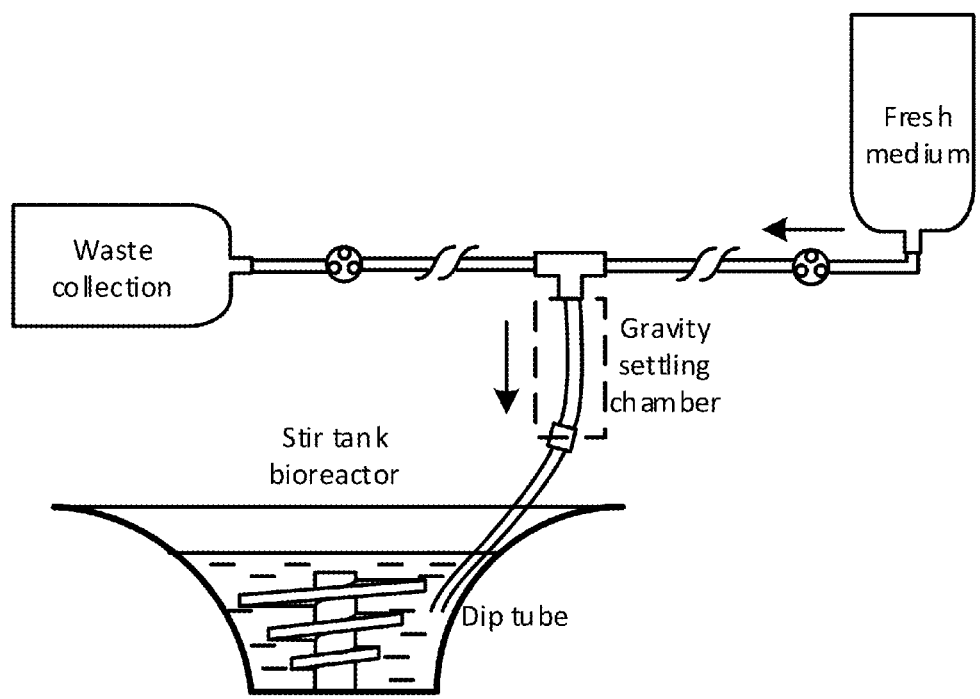
FIG. 4 shows a diagram of the tubing assembly for gravity settling and medium exchange in stirred tank bioreactors in which fresh medium is being added to the bioreactor in a slanted orientation.

Materials: Aggregates were cultured in a GE prototype stirred tank reactor depicted in FIGS. 3-4. Hyclone Labtainer bags were used to hold fresh medium for feed as well as to collect spent medium. Accutase™ was purchased from MP Biomedical (CA, USA); mTeSRTM1 medium was purchased from STEMCELL™ Technology Inc. (Vancouver, BC, Canada). Y-27632 (ROCK Inhibitor) was purchased from Sigma Aldrich (St. Louis, Mo.). CT2 hESC were obtained from Ren-He Xu at the University of Connecticut Health Center. The polygonal grid slicers and the tubing assembly for gravity settling used for passaging were manufactured specifically for this application and were not purchased through a commercial vendor.

Methods: Human embryonic stem cells were adapted from Matrigel™ to suspension aggregates for greater than 5 passages prior to stirred tank reactor experiments. Stock cells were confirmed to be karyotypically normal. Serial passaging was performed using Accutase™ to reduce aggregates to small clusters and single cells which reformed suspension aggregates after seeding. Cell counts and viability were determined using a Nucleocounter® NC200™ (Chemometec, Denmark).

The human embryonic stem cell line CT2 was suspension adapted from feeder-free cell stocks and maintained for at least 5 passages at small scale prior to bioreactor culture. Enzymatic passaging using Accutase™ produced a population of single cells and small (<5 cell) clusters. Aggregates formed 2-12 hours after addition of single cells/small clumps to the vessel. The cells formed aggregates between about 50 and 200 um diameter. It was normal to obtain a distribution of aggregate diameters 50 um above and below the mean aggregate diameter. The majority of aggregates fell within that size range, however there were on occasion some larger aggregates of roughly 200 to 400 um that formed. Conditions that favor smaller aggregates are preferred as nutrient availability can be limited in larger aggregates, and the smaller aggregates provide a greater relative expansion in the culture.

The preferred conditions provide spherical aggregates with minimal clumping. It is important to balance the level of agitation in the bioreactor, as too much agitation will lead to shearing including deformation of aggregates and producing excessive numbers of non-aggregated single cells. Too little agitation will lead to clumping of aggregates.

Not all pluripotent cell lines prefer the same culture conditions. The following parameters were used for PSC expansion, and those skilled in the art will recognize that other conditions will also provide PSC expansion in similar vessels: Temperature 37 degrees C., $CO_2$ level 5%, ambient O2 (~21%) or a reduced $O_2$ level, continuous or discontinuous stir speed of 40 rpm.

Tubing Assembly for Gravity Settling and Medium Exchange in Non-Perfusion Bags:

The conceptual construct of the tubing assembly on a stirred tank bioreactor is shown in FIGS. 1-4. The assembly provides the following functions including but not limited to the following: (1) removal of cell/cell culture medium mixture, (2) cell aggregate separation from outgoing cell culture medium, (3) cell culture medium addition, and (4) cell culture medium removal.

Removal of cell aggregate/cell culture medium mixture is accomplished through the use of a dip tube. The dip tube should be of sufficient length/orientation such that cells/media can be removed from the bioreactor while it is installed and in operation. Cell aggregate separation from outgoing media is achieved by the introduction of a gravity settling chamber with sufficient length (height) and diameter to ensure adequate gravity setting during media removal. The design of this chamber is not limited to a large diameter tube; a tortuous path may also be integrated if necessary for satisfactory cell aggregate separation. One or more than one tubing assemblies operating in parallel could be associated with the bioreactor to increase the rate of medium removal/addition. Tubing for fluid addition/removal needs to be of adequate length to ensure attainment of connections to media/waste containers. Fluid removal is achieved by pulling out the medium through the fluid removal path while keeping the fluid addition path closed. Fluid addition is achieved by instilling fresh medium through the fluid addition path while keeping the fluid removal path closed. The conceptual design in FIGS. 1-4 depicts a discontinuous perfusion method in which there is alternating medium removal and medium addition. Another embodiment of the concept is a continuous perfusion method in which separate tubing is used for filterless medium removal and medium addition.

For discontinuous perfusion, the software controls regulate the removal of a specific amount of spent medium and the addition of fresh medium. This approach is typically independent of the vessel weight. Preferably, a predefined volume of spent medium is removed followed by bolus addition of a volume of fresh medium, according to a pre-defined feeding schedule. For example, the feeding schedule could be set to remove 50 mL of spent medium every 2 hours, followed by an addition of 50 mL of fresh medium.

Filterless perfusion from stirred tank bioreactor. CT2 human embryonic stem cells at about 600,000 cells per mL (about 97% viability) were cultured as suspension aggregates in 250 mL in the GE prototype stirred tank bioreactor, and agitated at about 40 rpm. In other experiments, suspension aggregates were agitated at between 40 and 75 rpm. The aggregate sizes in the bioreactor ranged from about 100 um to about 300 um (FIG. 12). The gravity settling chamber was inclined at about a 45 degree angle and ran along the inner edge of the bioreactor. The tubing inner diameter was 3/32". The design of the filterless perfusion assembly was depicted as in FIGS. 3 and 4, and enabled both spent medium removal and fresh medium addition. Fresh medium addition in the same tubing dispaced any aggregates retained in the tubing back into the main bioreactor chamber. About 150 mL/day was exchanged using flow rates of 0.2 ml/min to 0.4 mL/min to remove medium from the bioreactor and 8 mL/min for fresh medium addition. Medium exchange was not continuous; instead 30 mL was exchanged 5 times per day. At the end of the culture, only 13 million cells (predominantly single cells) were found in the waste at 45% viability demonstrating very little loss of cells in the waste.

Slicer Design:

The slicer can be composed of a variety of biocompatible materials. The material must be amenable to sterilization, and have mechanical strength that allows it to withstand the stress experienced during flow of the cellular samples. The two materials tested for pluripotent stem cell aggregate passaging were nickel alloy and silicon. Those skilled in the art will recognize that other materials have properties that enable the desired slicer performance for aggregate passaging. The slicer is designed with a polygonal grid-like pattern, for example a square or hexagonal grid, with spacing between the walls of the grid between 50 microns and 400 microns. In some experiments, the slicer was coated with a hydrophobic material to reduce shearing and fouling. For the pluripotent stem cell aggregate passaging experiments described below, square and hexagonal grids with 100 um spacing were used. The slicer was mounted in line with tubing that permitted the sterile flow of aggregates through the tubing and across the slicer in a closed system. The slicer may be integrated into the closed system by various fastening mechanisms including, but not limited to adhesive, molten polymer flow, or clamping. In a preferred method, aggregates are maintained in suspension via a circulation loop driven by a pump and an in line conical bag (FIG. 8). Tubing leading to the slicer is connected to the main circulation loop, and a fraction of the cell aggregates in the circulation loop is delivered to the slicer through a second pump operating at a lower speed than the pump controlling the circulation loop. The sliced aggregates can be collected in a separate vessel, or reintroduced into the same vessel.

Slicer Performance During Cellular Aggregate Passaging:

Aggregates were passed across the slicer in a flow stream consisting of 100 mL to 1 L volumes. A benefit of the slicer compared to enzymatic passaging is a reduction in time, labor and reagents. Successful slicing down to roughly 100 um dimension was achieved by one or more passes through the slicer in a unidirectional or bidirectional flow. The flow rate was controlled to minimize shear. Aggregate slicing performance for size reduction, maintenance of cell viability and subsequent expansion were demonstrated on pluripotent stem cell aggregates passed through the slicer at flow rates of 15 to 150 mL/min. Those skilled in the art will recognize that good performance can also be achieved at other flow rates. The cell aggregate concentration used to pass through the slicer was determined to influence the recovery of sliced cell aggregates at high viability. Fouling of the slicer can result in reduced cell recovery and viability. It was determined that slicing of cell aggregate concentrations below about 3×10^6 cells per mL produced higher viability samples with higher recovery than cell concentrations greater than about 3×10^6 cells per mL. Fouling was minimized by maintaining a uniform suspension of aggregates in the flow stream, for example by using the mixing device shown in FIG. 8, resulting in higher cell viability and recovery. Sample images of sliced aggregates are shown in FIG. 9. The aggregate morphology after slicing includes irregular shapes, cuboidal shapes and spherical shapes. For 100 um slicers, at least one dimension of the aggregate is reduced to roughly 100 um diameter. Sliced aggregates were cultured in mTeSR1 and optionally 1 to 10 uM Y27632 ROCK inhibitor and allowed to expand. Y27632 ROCK inhibitor was not required for expansion of sliced pluripotent stem cell aggregates, unlike enzymatically passaged pluripotent stem cell aggregates which generally requires agents such as Y27632 ROCK inhibitor to maintain the viability of single pluripotent cells. The morphology of the sliced aggregates rapidly reformed a spherical shape under culture conditions. The expansion rate of sliced aggregates was similar to the expansion rate of enzymatically passaged cells (FIGS. 10 and 11). Aggregates can be passaged by the slicer without PBS wash required for enzymatic passaging, therefore passaging by slicing takes less time and less overall effort than enzymatic passaging. Those skilled in the art will recognize that the slicer function and performance is not dependent upon the Xuri Cellbag bioreactor platform, and is compatible with other types of bioreactors including but not limited to other rocking motion, spinning motion or orbital motion platforms or stirred tank bioreactors.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for culturing cells in a closed system, where the closed system comprises a cell culture vessel, a tubing assembly, a device for mixing cell aggregates, and a slicer grid, the method comprising:
providing the cells to the cell culture vessel;
expanding the cells in the cell culture vessel to generate the cell aggregates in the cell culture vessel;
conducting an automated perfusion of the cell aggregates in the cell culture vessel;
retaining the cell aggregates in the cell culture vessel by gravity settling of the cell aggregates during the perfusion;
harvesting the cell aggregates, and
conducting a serial passaging of the harvested cell aggregates in the closed system,
wherein the step of serial passaging comprises dissociating the harvested cell aggregates with the slicer grid mounted in line with a tubing of the tubing assembly and the device for mixing the cell aggregates.

2. The method of claim 1, wherein the serial passaging in the closed system is carried out in presence of a Rho-associated protein kinase (ROCK) inhibitor.

3. The method of claim 1, wherein the serial passaging in the closed system is carried out substantially in absence of an agent which maintains viability of passaged, monodispersed or disaggregated pluripotent cells.

4. The method of claim 3, wherein the agent which maintains the viability of passaged, monodispersed or disaggregated pluripotent cells is a Rho-associated protein kinase (ROCK) inhibitor.

5. The method of claim 1, wherein the cell aggregates which are expanded comprise human pluripotent stem cells.

6. The method of claim 1, wherein the cell culture vessel is a stirred tank bioreactor.

7. The method of claim 1, wherein said automated perfusion is carried out in the closed system without human intervention.

8. The method of claim 1, wherein the gravity settling chamber is at least 1 cm in length and positioned in an orientation that drives gravity settling of cell aggregates.

9. The method of claim 1, wherein the automated perfusion is conducted at a rate that allows gravity settling of cell aggregates of about 100 micron to about 800 micron diameter.

10. The method of claim 1, wherein an average diameter of each expanded cell aggregate is no more than about 800 micron in size.

11. The method of claim 1, wherein an average diameter of each expanded cell aggregate is no more than about 500 micron in size.

12. The method of claim 1, wherein a volume of the culture vessel is from about 50 mL to about 100 L.

13. A method for culturing cells in a closed system, where the closed system comprises a stirred tank bioreactor vessel, a tubing assembly, a device for mixing of cell aggregates, and a slicer grid, the method comprising:
providing the cells to the stirred tank bioreactor vessel;
expanding the cells in the stirred tank bioreactor vessel to generate cell aggregates;
conducting an automated perfusion of the cell aggregates in the stirred tank bioreactor vessel;
retaining the cell aggregates in the stirred tank bioreactor vessel by gravity settling of the cell aggregates during the perfusion;
harvesting the cell aggregates; and
conducting a serial passaging of the harvested cell aggregates in the closed system,
wherein the step of serial passaging comprises dissociating the harvested cell aggregates with the slicer grid mounted in line with the tubing of the tubing assembly and the device for mixing the cell aggregates.

14. The method of claim 13, wherein the serial passaging in the closed system is carried out substantially in absence of an agent which maintains viability of passaged, monodispersed or disaggregated pluripotent cells.

* * * * *